(12) United States Patent
Merel

(10) Patent No.: US 9,384,321 B2
(45) Date of Patent: Jul. 5, 2016

(54) ORGANIZATION, VISUALIZATION AND UTILIZATION OF GENOMIC DATA ON ELECTRONIC DEVICES

(75) Inventor: Patrick Merel, San Diego, CA (US)

(73) Assignee: PORTABLE GENOMICS, INC., San Diego, CA (US)

( * ) Notice: Subject to any disclaimer, the term of this patent is extended or adjusted under 35 U.S.C. 154(b) by 334 days.

(21) Appl. No.: 13/989,737

(22) PCT Filed: Nov. 23, 2011

(86) PCT No.: PCT/US2011/062134
§ 371 (c)(1),
(2), (4) Date: Oct. 11, 2013

(87) PCT Pub. No.: WO2012/071564
PCT Pub. Date: May 31, 2012

(65) Prior Publication Data
US 2014/0033125 A1    Jan. 30, 2014

Related U.S. Application Data

(60) Provisional application No. 61/417,247, filed on Nov. 25, 2010.

(51) Int. Cl.
*G06F 15/00*    (2006.01)
*G06F 13/00*    (2006.01)
(Continued)

(52) U.S. Cl.
CPC .............. *G06F 19/28* (2013.01); *G06F 3/0482* (2013.01); *G06F 3/0485* (2013.01); *G06F 19/26* (2013.01)

(58) Field of Classification Search
CPC ............................... G06Q 50/24; G06F 19/322
USPC ................... 715/700, 761–765, 751, 851–853
See application file for complete search history.

(56) References Cited

U.S. PATENT DOCUMENTS

| | | | |
|---|---|---|---|
| 7,560,637 | B1 | 7/2009 | Robbin et al. |
| 2004/0093331 | A1* | 5/2004 | Garner et al. ..................... 707/3 |

(Continued)

FOREIGN PATENT DOCUMENTS

| | | |
|---|---|---|
| CN | 1744080 A | 3/2006 |
| CN | 1784498 A | 6/2006 |

(Continued)

OTHER PUBLICATIONS

Chen et al., GWAS GUI: graphical browser for the results of whole-genome association studies with high dimensional phenotypes. Bioinfomatice (online). 25(2): 284-285 (2009).

(Continued)

*Primary Examiner* — Kevin Nguyen
(74) *Attorney, Agent, or Firm* — Wilson Sonsini Goodrich & Rosati

(57) ABSTRACT

Described herein are methods, devices and systems for simple organization, visualization and use of genome data (e.g. human genome data) on electronic devices (e.g. portable devices). In some embodiments, the data are organized and/or visualized according to phenotype traits, genes, and/or markers in a similar manner to the organization and/or visualization of digital music contents. This concept allows a new procedure for genomic data organization and facilitates the development of genomic data visualization tools. The methods described herein can be implemented with consumer-oriented software on electronic devices, computers, and portable devices, for the use of genomic related data in the field of personalized medicine for predictive, preventive and participative wireless healthcare.

19 Claims, 14 Drawing Sheets

(51) Int. Cl.
*G06F 19/28* (2011.01)
*G06F 19/26* (2011.01)
*G06F 3/0482* (2013.01)
*G06F 3/0485* (2013.01)

(56) References Cited

U.S. PATENT DOCUMENTS

2005/0158767 A1 7/2005 Haskell et al.
2006/0052945 A1 3/2006 Rabinowitz et al.
2010/0046842 A1 2/2010 Conwell

FOREIGN PATENT DOCUMENTS

EP 2643784 10/2013
WO WO 2009/046021 A1 4/2009
WO WO 2012/071564 5/2012

OTHER PUBLICATIONS

PCT/US2011/062134 IPRP dated Jul. 30, 2013.
PCT/US2011/062134 ISR and WO dated Mar. 28, 2012.
Chinese Patent Application No. 201180065443.3 First Office Action dated Sep. 6, 2015.

* cited by examiner

ORGANIZATION, VISUALIZATION AND UTILIZATION OF GENOMIC DATA ON ELECTRONIC DEVICES

CROSS-REFERENCE

This application claims the benefit of U.S. Provisional Application No. 61/417,247, filed Nov. 25, 2010, which application is incorporated herein by reference.

BACKGROUND OF THE INVENTION

Today, about 1,800 genetic tests are already on the market and every week between 5 and 10 new genetic tests are introduced. The continuing advent of such tests and the introduction of molecular diagnostics into the healthcare system are profoundly changing how medicine is practiced.

The most popular genomic tests being used today are addressing close to one million genetic markers including gene mutations and polymorphisms. While this is a large amount of data, it is still a small portion of our total genome information. Upcoming breakthrough technologies for genome sequencing are expected provide full genome sequencing at a very low cost (e.g. under $100) in the upcoming years, which should report even more data from 11 million potential markers (e.g., Single Nucleotide Polymorphisms, "SNP").

In the meantime, healthcare professionals and patients are being confronted with gene annotations and disease pathway data (i.e. 'omics' data) that are complex and difficult to identify and understand. Only molecular biology trained professionals are able to read and make use of such complex data sets, which limits access by both patients and clinical professionals. There is a need for improved methods of organizing, visualizing and utilizing genomic data.

Currently, the consulting of 'omics' data is made through software designed for molecular biologists or through web interfaces on personal computers. These methods tend to limit the use and sharing of genomic data in everyday life. There is no simple tool for carrying genomic data and sharing this information, including sharing between patients and physicians. There is a need for methods of organizing, visualizing and utilizing genomic data on portable devices.

SUMMARY OF THE INVENTION

Described herein are new methods, devices and systems for simple organization, visualization and use of genome data (e.g. human genome data) on electronic devices (e.g. portable devices).

One embodiment provides a graphical user interface (GUI) for displaying genomic information on a mobile device, the GUI comprising; a listing of phenotypic traits, diseases, or a combination thereof; a listing of genes; and a listing of genetic markers, wherein the genetic markers comprise metadata comprising: a default map location; a nucleotide UID; and a gene ontology, whereby selecting a phenotypic trait or disease from the list thereof displays a listing of genes and/or genetic markers correlated with the selected phenotypic trait or disease.

Another embodiment provides a GUI wherein the metadata further comprises one or more of: a disease name, a phenotype, a gene name, a protein name, a chromosome, a nucleotide accession, a protein accession, a protein UID, a EC/RN number, a filter, a locus link ID, a MIM, a modification date, a property, a PubMed UID, a taxonomy ID, a text word, and a UniGene cluster number.

Another embodiment provides a GUI wherein the phenotypic traits, diseases, or a combination thereof are represented by images.

Another embodiment provides a GUI wherein the images further comprise genes and/or genetic markers correlated with the phenotypic trait or disease.

Another embodiment provides a GUI wherein the images are scrollable by touching the display of the mobile device with a vertical, horizontal, or circular motion.

Another embodiment provides a GUI wherein the images further comprise an indication when the phenotypic trait or diseases is clinically relevant in an individual.

Another embodiment provides a GUI wherein the indication is a color code.

Another embodiment provides a GUI wherein the genomic information is from an individual person.

Another embodiment provides a GUI wherein the genomic information is obtained from public databases.

Another embodiment provides a GUI wherein the correlations are obtained from public databases and/or scientific literature.

Another embodiment provides a method for displaying genomic information on a mobile device, the method comprising populating a multimedia database viewable by a graphical user interface (GUI) with genomic information in place of multimedia information, whereby operation of the GUI displays genomic information.

Another embodiment provides a method wherein: an album title field is populated with a listing of phenotypic traits, diseases, or a combination thereof; an artist field is populated with a listing of genes; and a title track field is populated with a listing of genetic markers, whereby selecting a phenotypic trait or disease from the list thereof displays a listing of genes and/or genetic markers correlated with the selected phenotypic trait or disease.

Another embodiment provides a method wherein the method, further comprises one or more of: activating an application on the mobile device based on the genomic information; and integrating geolocation information of the mobile device with the genomic information.

Another embodiment provides a genomic information database structure, wherein the container is a phenotypic trait, disease, or combination thereof, and wherein the database further comprises genes, genetic markers, default map locations, nucleotide UID, and gene ontology information.

Another embodiment provides a method for creating a portable genomic dataset for an individual, the method comprising: obtaining a set of genetic markers of the individual in a computer readable format; attributing a probability of expression of one or more phenotypic traits for each genetic marker by comparing each genetic marker with a correlation between the phenotypic trait and the genetic marker in a population of individuals; assembling sets of genetic markers related to each phenotypic trait; optionally calculating the probability of expression of the phenotype; and producing a portable genomics data set comprising only the information about phenotypic traits expected to be expressed by the individual, the relevant genetic markers, and the probability of expression of the phenotypic trait.

Another embodiment provides a portable electronic device configured to display the GUI described herein.

Another embodiment provides a portable electronic device configured to perform the methods described herein.

Another embodiment provides a portable electronic device comprising the genomic information database structure described herein.

Another embodiment provides a portable electronic device encoding the portable genomic dataset described herein.

Another embodiment provides the portable electronic device, wherein the device is a mobile phone, personal digital assistant (PDA), or tablet computer.

Another embodiment provides the use of the methods or the portable electronic devices described herein to schedule a medication dosage regimen, and/or monitor compliance thereof.

Another embodiment provides the use of the methods or the portable electronic devices described herein to share genomic information with medical professionals.

Another embodiment provides the use of the methods or the portable electronic devices described herein to schedule medical appointments or consult medical specialists.

Another embodiment provides the use of the methods or the portable electronic devices described herein to facilitate financial transactions based on genomic information.

Another embodiment provides the use of the methods or the portable electronic devices described herein to predict the efficacy of a drug and/or to predict side-effects of a drug.

Another embodiment provides the use of the methods or the portable electronic devices described herein in combination with geolocation features of the portable electronic device to determine the relative contribution of genetics and environment on a phenotypic trait or disease.

Another embodiment provides the use of the methods or the portable electronic devices described herein by two individuals in order to determine the last common ancestor shared by the individuals.

Another embodiment provides the use of the methods or the portable electronic devices described herein by a male individual and by a female individual in order to determine the probability of phenotypic traits and/or diseases being expressed in the offspring produced by the male and female individuals.

Another embodiment provides a method wherein the genetic markers are single nucleotide polymorphisms (SNPs), micro-satellites, DNA methylation patterns, histone deacetylation patterns, or any combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
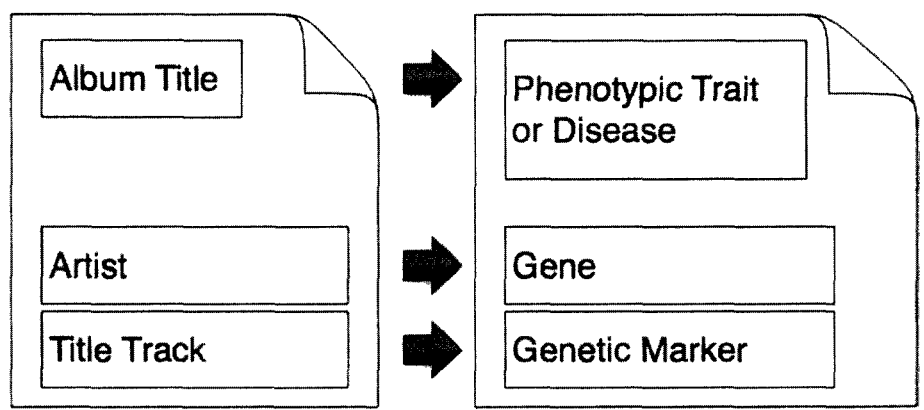
FIG. 1 shows an embodiment for the manipulation of genomic data like digital music.

Described herein are methods, devices and systems for simple organization, visualization and use of genome data (e.g. human genome data) on electronic devices (e.g. portable devices). In some embodiments, the data are organized and/or visualized according to phenotype traits, genes, and/or markers in a similar manner to the organization and/or visualization of digital music contents. This concept allows a new procedure for genomic data organization and facilitates the development of genomic data visualization tools. The methods described herein can be implemented with consumer-oriented software on electronic devices, computers, and portable devices, for the use of genomic related data in the field of personalized medicine for predictive, preventive and participative wireless healthcare.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Genomic Data

"Genomic" and "genetic" are herein used interchangeably and mean of or relating to genes. Examples of genomic data are phenotypic traits, genes, and genetic markers.

Genomic data are available from public or private databases and academic or commercial diagnostic laboratories. Genomic data can also be obtained by sequencing the entire genome of an individual, or a portion thereof. Suitable methods of DNA sequencing include Sanger sequencing, polony sequencing, pyrosequencing, ion semiconductor sequencing, single molecule sequencing, and the like. Sequenced genomic data can be provided as electronic text files, html files, xml files and various other regular databases formats.

Genomic data includes sequences of the DNA bases adenine (A), guanine (G), cytosine (C) and thymine (T). Genomic data includes sequences of the RNA bases adenine (A), guanine (G), cytosine (C) and uracil (U). Genomic data also includes epigenetic information such as DNA methylation patterns, histone deacetylation patterns, and the like.

"Phenotypic traits" are an organism's observable characteristics, including but not limited to its morphology, development, biochemical or physiological properties, behavior, and products of behavior (such as a bird's nest). Phenotypic traits also include diseases, such as various cancers, heart disease, Age-related Macular Degeneration, and the like.

"Genes" are locatable regions of genomic sequence corresponding to a unit of inheritance, which is associated with regulatory regions, transcribed regions, and or other functional sequence regions. A gene is a molecular unit of heredity of a living organism. Exemplary genes are the CFH gene, C2 gene, LOC387715/ARMS2, and the like.

"Genetic markers" are genes, portions of genes, DNA sequences, and the like that can be used to identify cells, individuals, or species. Genetic markers can be described as genetic variations within a population and may be correlated with phenotypic traits. Single nucleotide polymorphisms ("SNP") are single DNA base pair changes and are an example of a genetic marker. Exemplary genetic markers include rs1061147, rs547154, rs3750847, and the like.

Organization of Genomic Data

In some embodiments, genomic data are organized according to a new procedure. The procedure consists of substituting digital music information for genomics information.

In one aspect, genomic data are organized and/or visualized using the user interface ("UI") of existing digital music applications. In other aspects, genomic data are organized and/or visualized using a user interface that is similar to existing digital music applications. The user interface is a simple graphical user interfaces (GUI) in some embodiments. In some embodiments, phenotypic traits are preferably stored and/or viewed as music albums. In other embodiments, phenotypic traits are stored and/or viewed as music artists or music tracks. In some embodiments, genes are preferably stored and/or viewed as music artists. In other embodiments, genes are stored and/or viewed as music albums or music tracks. In some embodiments, genetic markers are preferably stored and/or viewed as music tracks. In other embodiments, genetic markers are stored and/or viewed as music albums or music artists.

One GUI of an existing digital music application suitable for use as described herein is described in U.S. Pat. No. 7,560,637. In one embodiment, the album title field of the database described in U.S. Pat. No. 7,560,637 is populated with phenotypic traits and/or diseases, the artist field of the database described in U.S. Pat. No. 7,560,637 is populated with genes, and the title track field of the database described in U.S. Pat. No. 7,560,637 is populated with genetic markers.

Procedure for Creating a Genomic Data Set

Figure 2:
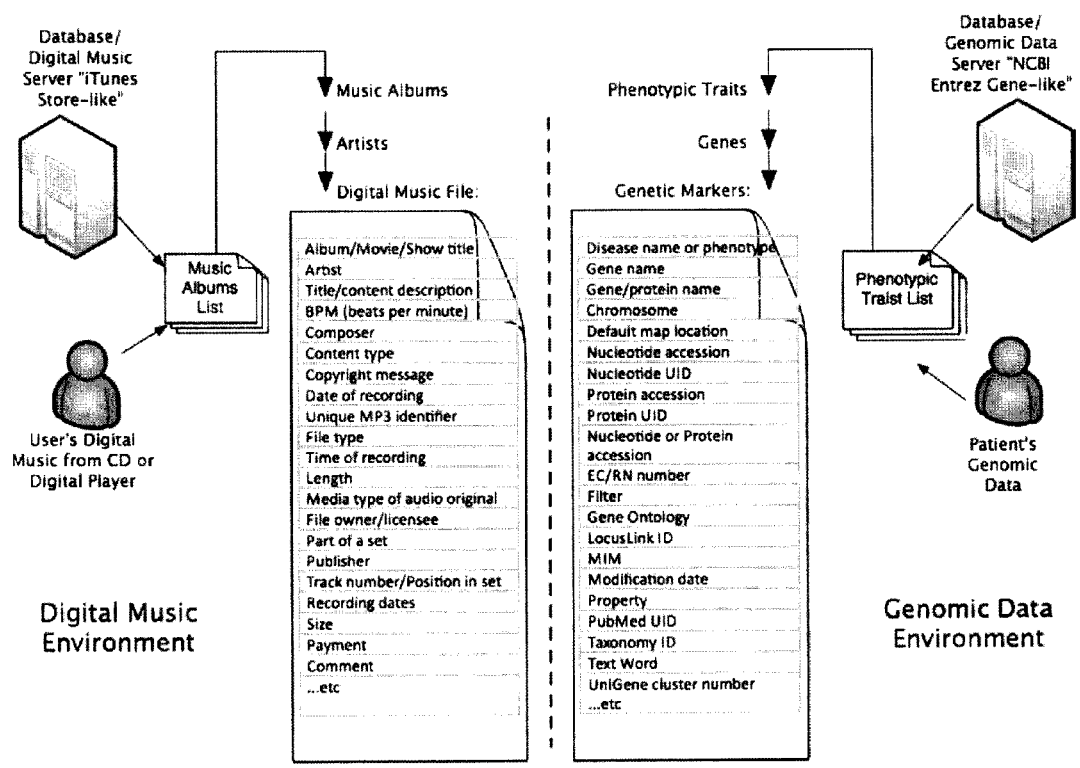
FIG. 2 shows an embodiment for the manipulation of genomic data like digital music.
Figure 3:
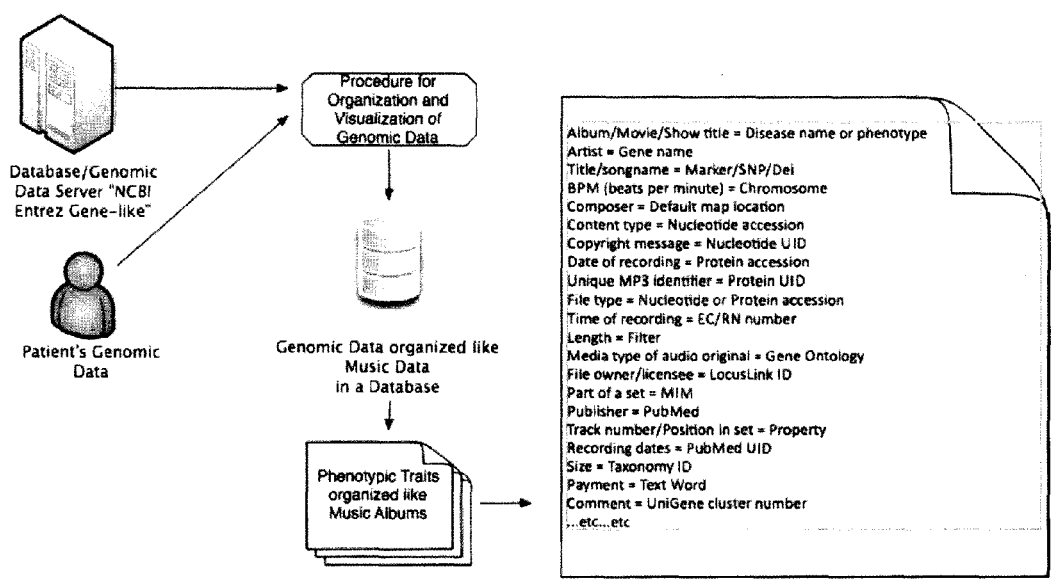
FIG. 3 shows an embodiment for the manipulation of genomic data like digital music.

FIGS. 1, 2 and 3 show the procedure for the substitution of genomic data in place of digital music data. Turning to FIG. 1, in some embodiments, phenotypic traits are substituted for music albums, genes are substituted for music artists, and genetic markers are substituted for music tracks.

In particular, exemplary steps for organizing genomic data comprise:
1. Obtaining the genotype of a person in the form of an electronic file. The genotype may contain sequences of a limited number of genetic loci or the complete assembly of the genome.
2. Identify the genetic markers associated with phenotypic traits as described in the scientific literature, in databases, in publicly accessible or in institutional databases, in academic or privately held databases, and the like.
3. For each genotypic element retained, attribute a probability of expression of one or more phenotypic traits. These probabilities may be adjusted to the particular ethnic group of the person as derived by the study of pertinent genetic markers contained in the entire genomic dataset.
4. Assemble sets of genetic markers related to each pertinent phenotypic trait and, if necessary, calculate de novo the probability of expression of the phenotype.
5. Produce a new dataset (herein arbitrarily named the "Portable Genomics" data set) containing only the information about phenotypic traits expected to be expressed by the person, the relevant genetic markers and the probability of expression of the phenotypic trait.

Procedure for Organizing Genomic Data

In some embodiments, the Portable Genomics dataset is used to prepare the display of pertinent personal data. In particular, exemplary steps include:
6. Organize genomic data in a database whose structure is similar to digital music databases structure.
7. Store phenotypic traits, genes, or genetic markers but preferentially phenotypic traits, in a music album data field.
8. Store phenotypic traits, genes, or genetic markers but preferentially genes, in an artist data field.
9. Store phenotypic traits, genes, or genetic markers but preferentially genetic markers, in a track data field.
10. Define the phenotypic trait, the gene, or the genetic marker but preferentially the genetic marker as the container for the related fields described in steps (7), (8) and (9).
11. Include genomic information (metadata) to the database. The metadata can be stored in an ID3 format container, as is done with digital music. Metadata fields can be adapted from the digital music world to the genomics field, e.g. by replacing the field dedicated to «music genre» with a field dedicated to «medical category», replacing the field «album cover image» with a field «phenotypic trait graphical image», and the like.

Procedure for Displaying Genomic Data

With genomic data structured according steps (6), (7), (8), (9), (10), and (11), the use and visualization of genomic data becomes possible on any kind of electronic device that is used to play or visualize digital music, but preferentially phones, smart phones and tablets. The procedure described herein can benefit from consumer based graphical user interfaces that are already available for digital music browsing on these electronic platforms.

In some embodiments, one transfers the database created according steps (6), (7), (8), (9), (10), and (11), to an electronic device, preferentially a phone, a smart phone or a tablet to do any one or more of:
    display phenotypic traits, genes, or genetic markers (but preferentially phenotypic traits) as a list of graphical images (similar to digital music album covers), optionally in vertical display mode or horizontal display mode;
    display phenotypic traits, genes, or genetic markers (but preferentially phenotypic traits) as graphical images (similar to digital music album covers), optionally in an horizontal or vertical cover-flow user interface or in an horizontal or vertical carrousel user interface;
    display various information by color coded tags or thumbnails on graphical images, optionally to enable rapid identification of clinically relevant information; and
    trigger wireless operations or actions based on genomic data information.

Public Databases

In some aspects, genetic markers may be obtained from databases such as the NCBI GenBank (http://www.ncbi.nlm.nih.gov) or the 1000 Genomes project (http://www.1000genomes.org/).

Use of Metadata

In one aspect, metadata are associated with the genomic information as described herein. FIG. 2 shows the use of metadata annotation of music files and their organization, compared to the possible organization of metadata annotation of genomic data and their organization. On the left side, music files are extracted from digital music servers or from user's CDs, computers or portable devices. They are stored into databases (music libraries of music tracks). Each track is identified according metadata embedded into each file. These metadata annotations allow rapid identification of music based on album title, artist name, track name, and the like. Following the substitution procedure proposed in FIG. 1, genetic markers information can be stored in a similar way. On the right side of FIG. 2, genomic marker information is extracted from specialized databases or from genomic test results. This data can be stored in a single database of genetic marker files, each file having metadata organized according the procedure described in FIG. 1. Genetic markers being substituted for the track name, their metadata may contain the gene's name (substituted for the artist name) and phenotypic traits they have an effect on (substituted for album name). As with music file metadata (shown on the left side), genetic marker metadata are not restricted to gene names and phenotypic trait names. Metadata can also include information like chromosome location, genetic map location, nucleotide accession number, locus link ID, and the like as shown in FIG. 2.

Turning now to FIG. 3, shown herein is the genomic data organization made possible by the methods described herein. Genomic data and genetic marker information can be collected from specialized databases or from a patient's personal data, processed according the procedure described in FIG. 1, and stored into a database of genetic markers. In some embodiments, each genetic marker is annotated with metadata related to genomic information.

The combined organization of phenotypic traits, genes, and genetic markers allows the use of existing digital music applications users interfaces (UI) and/or the development of simple graphical user interfaces (GUI) for browsing genomic data. In particular, it allows the use of interfaces from the digital music world, like album cover lists, cover-flow browsers, and the like, well known visualization tools in the consumer public. Finally, it brings the possibility of having simple genomic visualization tools on electronic devices, computers and portable devices like smart phones and tablets.

Portable Devices

Portable devices suitable for use in the methods described herein include mobile phones, personal digital assistants (PDAs), tablet computers, and the like. In some embodiments, the portable devices have touch sensitive screens and the graphical user interfaces described herein respond to touch.

Data Flow

Figure 4:
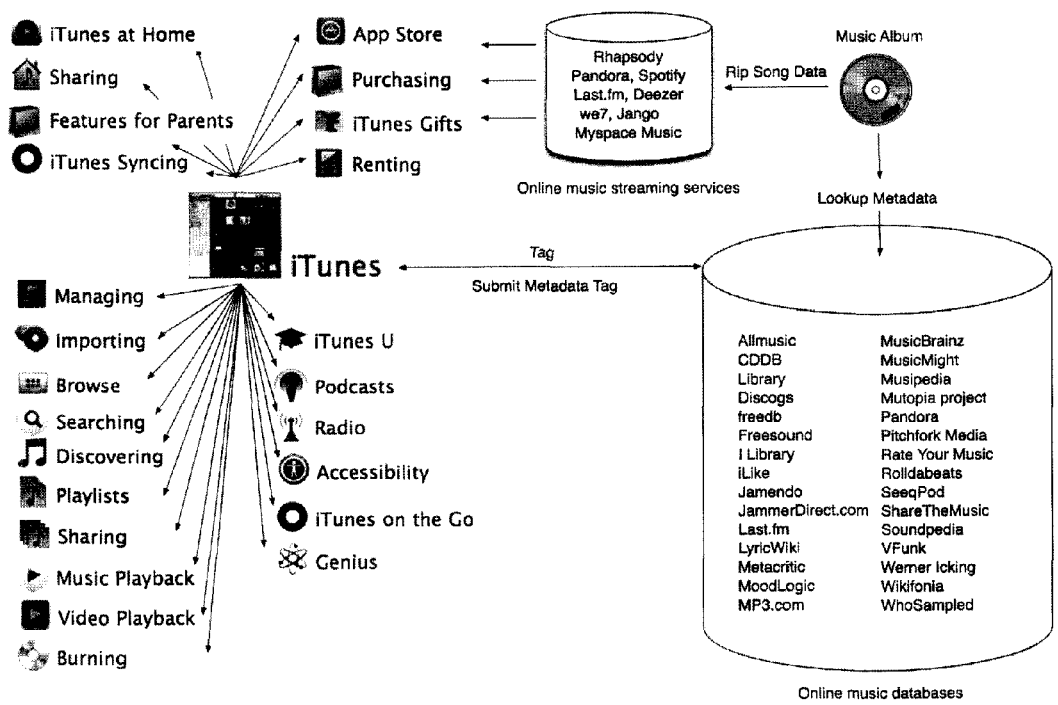
FIG. 4 shows the data flow for digital music.
Figure 5:
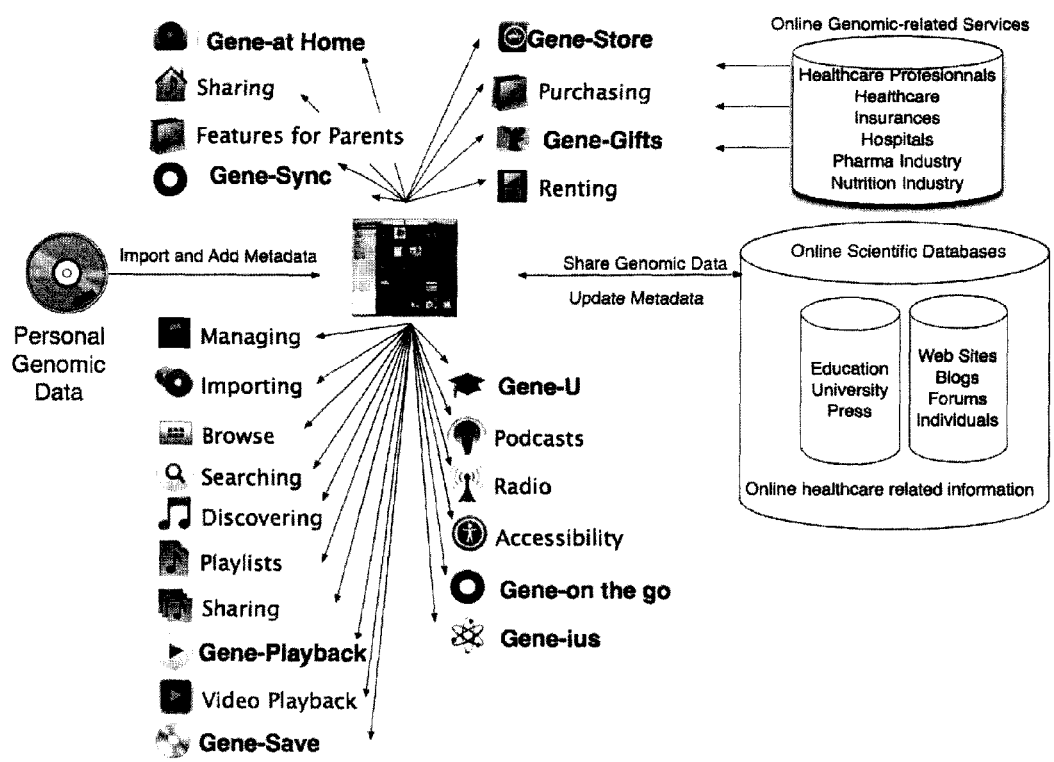
FIG. 5 shows the data flow for genomic data.

FIGS. 4 and 5 show the data flow in the digital music universe and how genomic data can use a similar flow in the genomic sciences universe as described herein.

FIG. 4 reproduces the example of a popular digital music universe as represented by Apple Computer Inc.'s (Cupertino, Calif.) iTunes environment. Music artists produce CD albums and music tracks are stored in databases, available to consumers through online services. The Apple's iTunes software provides a single interface on computers and portable devices to access and use music tracks, including radios, podcasts, academic courses and videos. The music track is at the center of this data flow.

FIG. 5 shows a similar universe transposed to a genomic data environment. Genomic information, genomic test results are organized according the procedure described in FIG. 1 and then stored in databases available through online services. The data flow based on genetic markers (e.g. music tracks) can then be used for various applications related to personalized medicine (named here Gene-at-Home, Gene-Store, Gene-Gifts), education and training in the field of genomics (named here Gene-U, podcast, radio), sharing and storage of personal genomic health records (named here Gene-Save, Gene-Playback, Gene-Sync) and even genomic based entertainment (named here Gene-on-the go, Gene-ius). The genetic marker is at the center of this data flow.

Graphical User Interface

Figure 6:
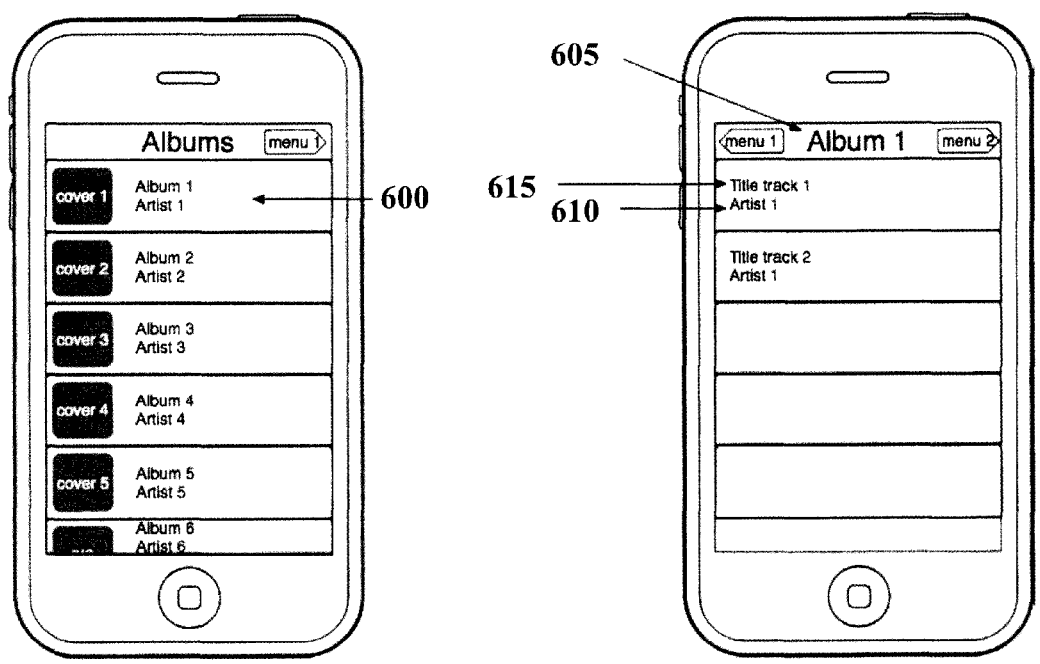
FIG. 6 shows a user interface for digital music browsing on portable devices.
Figure 7:
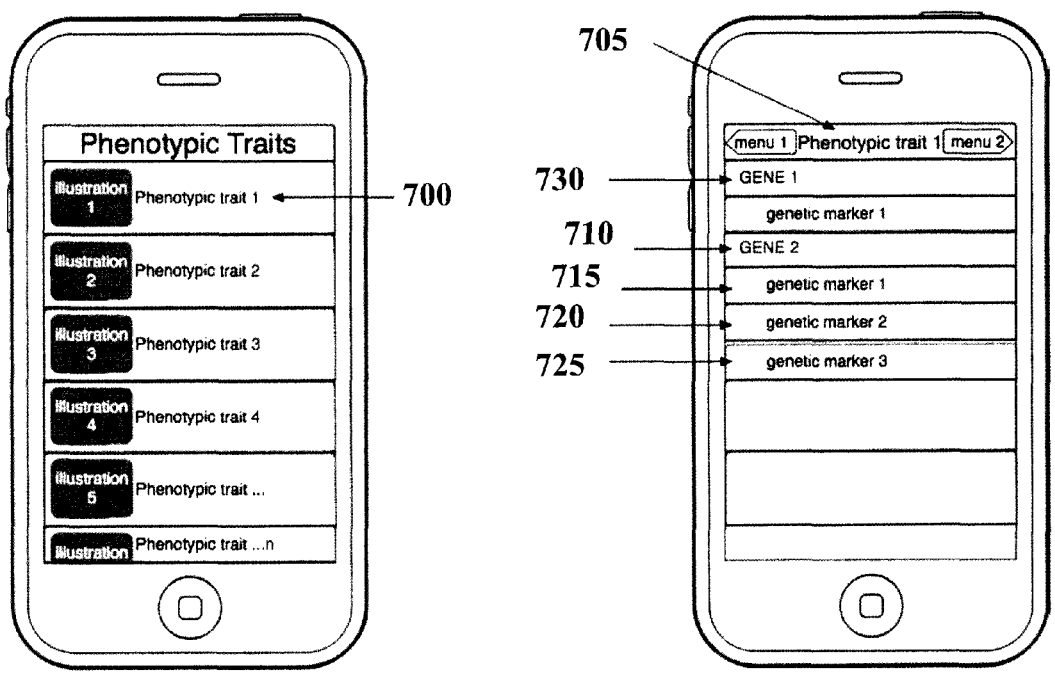
FIG. 7 shows an embodiment for genomic data visualization.

FIGS. 6 and 7 show the transposition of a major digital music browser interface to a genomic data browser as described herein.

FIG. 6 shows a popular interface for digital music browsing on portable devices. Shown here is the iTunes interface on Apple's iPhone™. In vertical mode, digital music browsers display list of music albums, including a picture of the album cover, album name and artist name. Touching the cover on the sensitive touch screen of the device (indication 600) opens a new screen with additional information related to this particular album, e.g. album name (indication 605), artist name (indication 610), title tracks (indication 615), and the like.

FIG. 7 shows the conversion of this type digital music browser to a genomic data browser as described herein. A list of phenotypic traits can be visualized on a vertical interface, using illustrations to identify phenotypic traits (indication 700). By touching the illustration, the phenotypic trait name or line will bring a new screen of information related to this particular phenotypic trait. Further information may include the trait's name (indication 705), gene or genes related to this particular trait (indications 710, and 730) and genetic markers participating into each gene (indications 715, 720, and 725).

Figure 8:
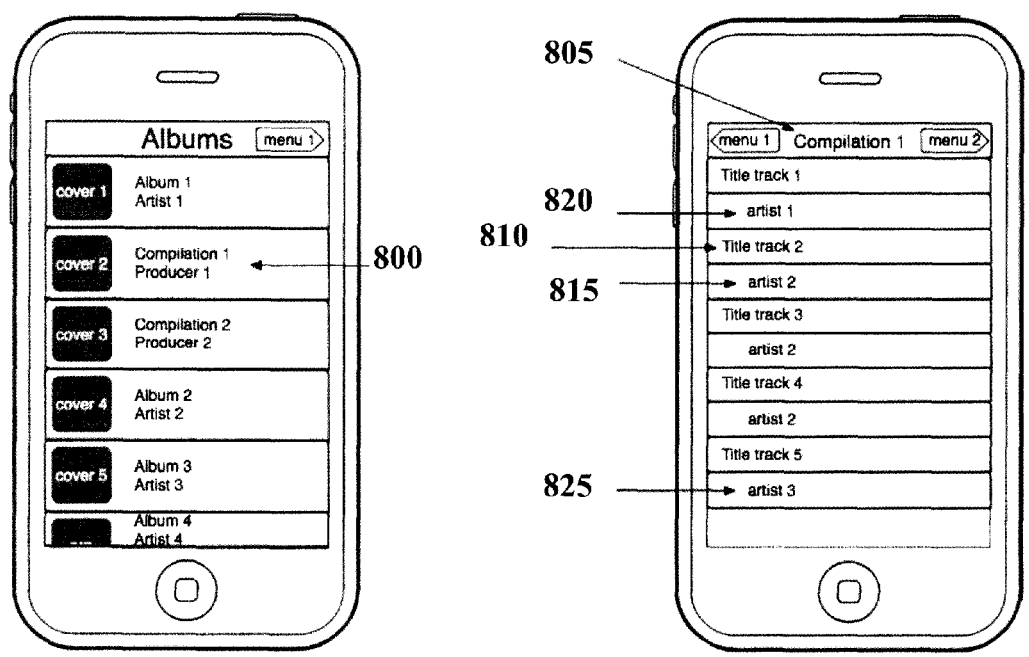
FIG. 8 shows a user interface on a portable device for complex digital music browsing.
Figure 9:
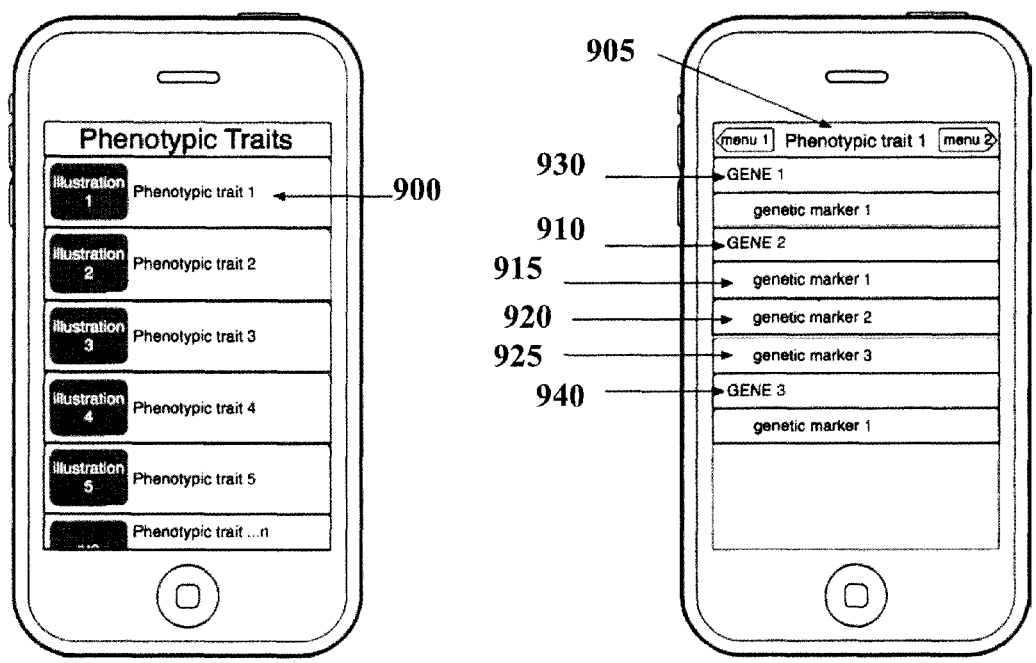
FIG. 9 shows an embodiment of a user interface on portable devices for complex genomic data visualization.

FIGS. 8 and 9 show how to use the procedure described herein to visualize complex genomic data on computer or portable devices.

FIG. 8 shows the display of complex digital music data (e.g. compilation of artists albums) on a portable device. A list of albums or compilation albums is shown on a vertical mode display. Touching the name or line for a compilation album (indication 800) on sensitive touch screens can reveal a complex list of data such as the compilation album name (indication 805), name of participating artists (indications 815, 820, and 825) and title track (indication 810).

FIG. 9 shows the display of complex genomic data on a portable device as described herein. A list of phenotypic traits, genes, or genetic markers (but preferentially phenotypic traits) (indication 900), is displayed in a vertical list mode. Touching the illustration, the phenotypic trait name or line will bring a new screen of information related to this particular phenotypic trait, such as the name of the trait (indication 905), the list of participating genes (indications 910, 930 and 940), the list of genetic markers located into each gene (indications 915, 920, 925).

Figure 10:
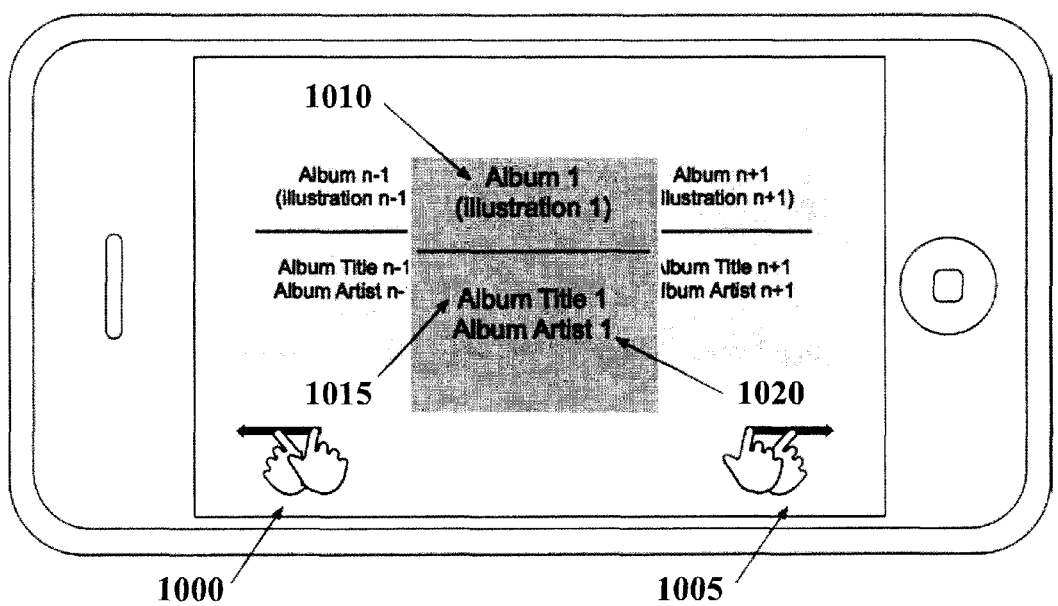
FIG. 10 shows a graphical user interface for digital music browsing.
Figure 11:
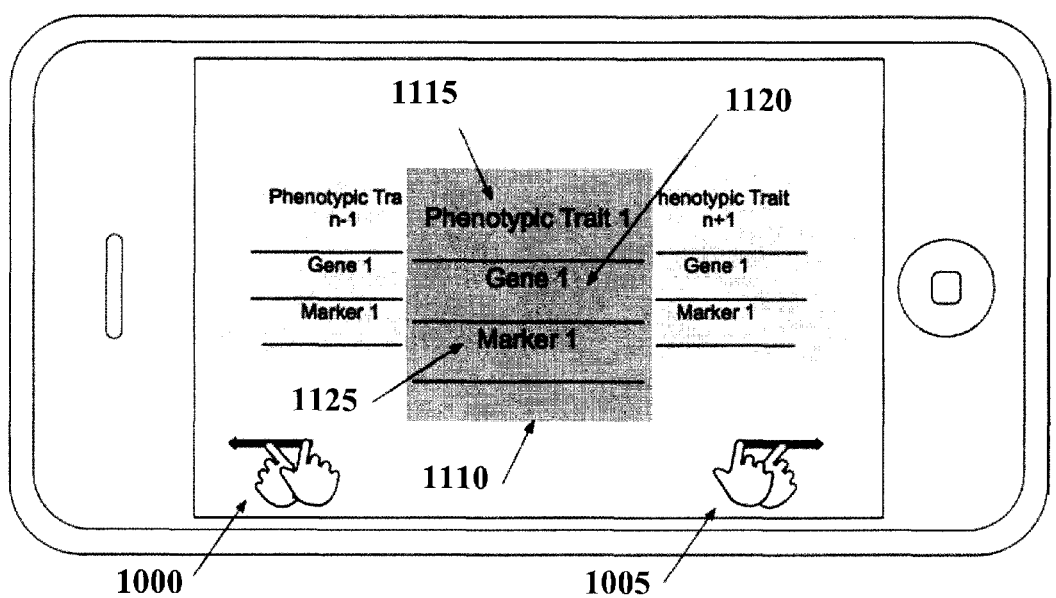
FIG. 11 shows an embodiment of a graphical user interface for genomic data graphical visualization.

FIGS. 10 and 11 show how to use the methods described herein to graphically visualize complex genomic data on computers or portable devices.

FIG. 10 shows the use of a cover-flow type of user interface for the visualization of digital music data. Music album cover images are displayed on a horizontal line and can be moved from left to right and vice-versa (indications 1000 and 1005), to reveal a large number of additional album cover images. Cover images can show part of the data (e.g. cover art (indication 1010), album name (indication 1015), artist name (indication 1020), and the like). A touch or a click on the cover can also reveal the back cover to present a set of additional data (e.g. composer, year of release, musical genre).

FIG. 11 shows the use of the horizontal cover-flow type of user interface for the visualization of genomic data. When genomic data are organized according the methods described herein, genomic data can be displayed graphically. Illustrations for phenotypic traits can be used in place of album covers on a vertical or horizontal graphical user interface and a long list of phenotypic traits can be browsed from left to right and vice-versa by clicking or touching the screen (indications 1000 and 1005). The graphical list of phenotypic traits can display either a related illustration (indication 1010) and/or genomic data like name of the phenotypic trait (indication 1115), the name of implicated genes (indication 1120), the name of participating genetic markers (indication 1125), and the like. Also, a touch or a click on the illustration (indication 1110) can reveal the back of the graphical illustration to present a complex set of additional data (e.g. genes location, genetic markers positions, bibliography, and the like).

Figure 12:
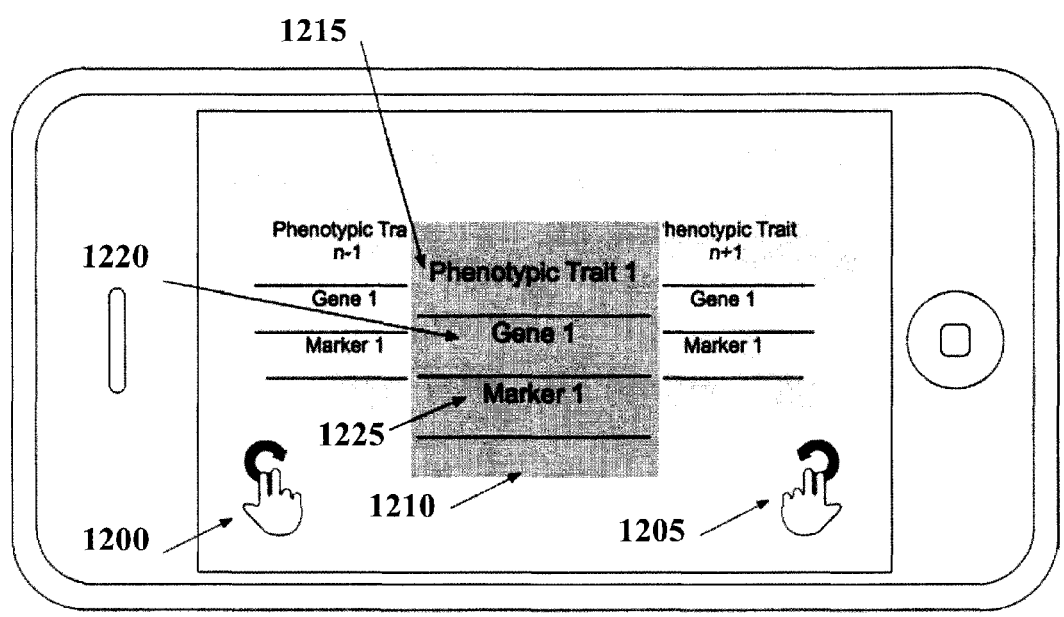
FIG. 12 shows an embodiment of a graphical user interface based on thumbnail images carousel that can be used for complex genomic data graphical visualization.

FIG. 12 shows the use of a carousel based user interface for genomic data display on computers or portable devices. This type of graphical user interface is frequently used for the display of digital images or digital music. It can be used for the display of genomic data when genomic data are organized according the methods described herein. A list of phenotypic traits can then be displayed as thumbnail images and the user can scroll through a large list of phenotypic traits by clicking or touching the screen with a circular left to right movement or vice-versa (indications 1200, 1205). The graphical list of phenotypic traits can display either a related illustration (indication 1210) and/or genomic data like name of the phenotypic trait (indication 1215), the name of implicated genes (indication 1220), the name of participating genetic markers (indication 1225), and the like. Also, a touch or a click on the illustration (indication 1210) can reveal the back of the graphical illustration to present a complex set of additional data (e.g. genes location, genetic markers positions, bibliography, and the like).

Figure 13:
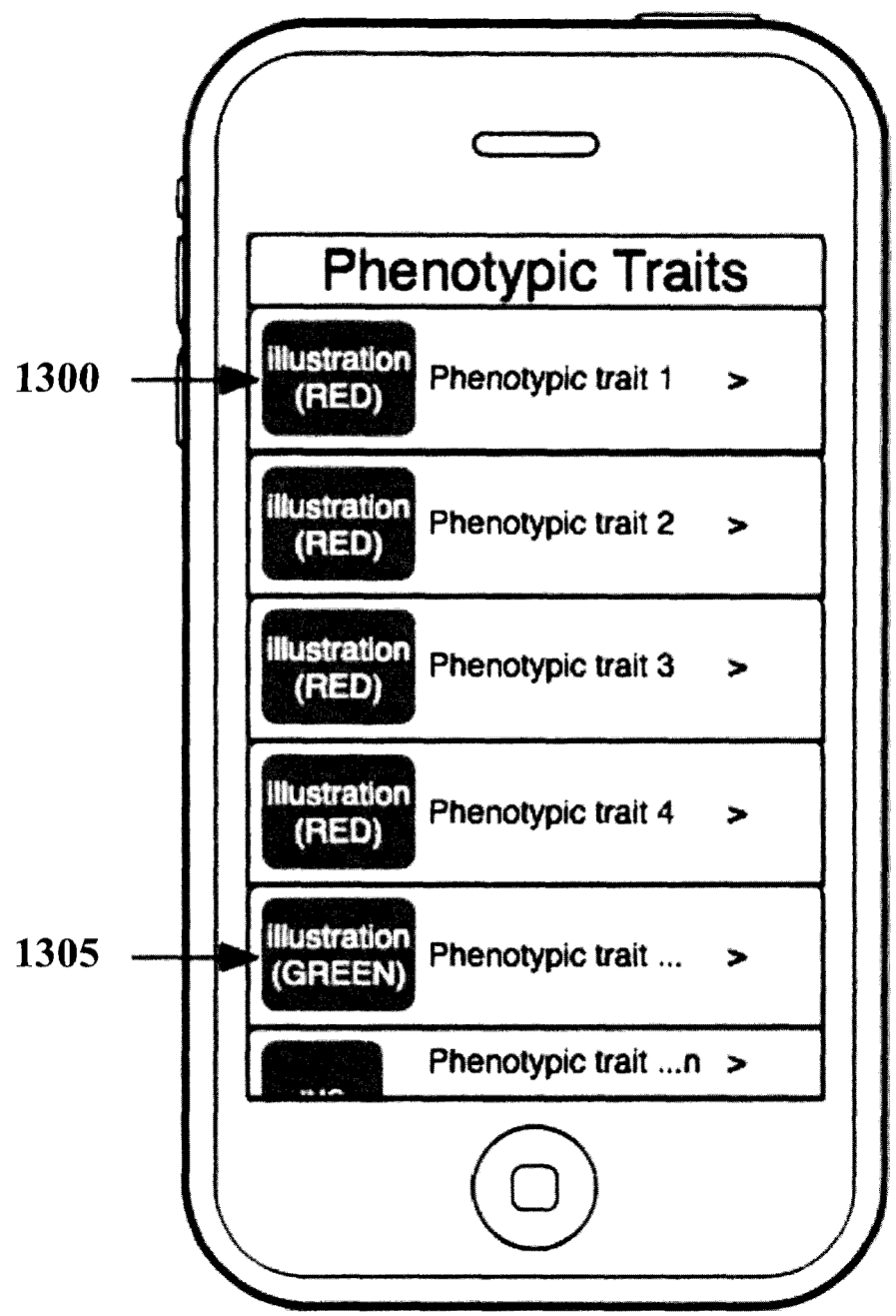
FIG. 13 shows an embodiment for the rapid identification of genomic data utility on portable devices.
Figure 14:
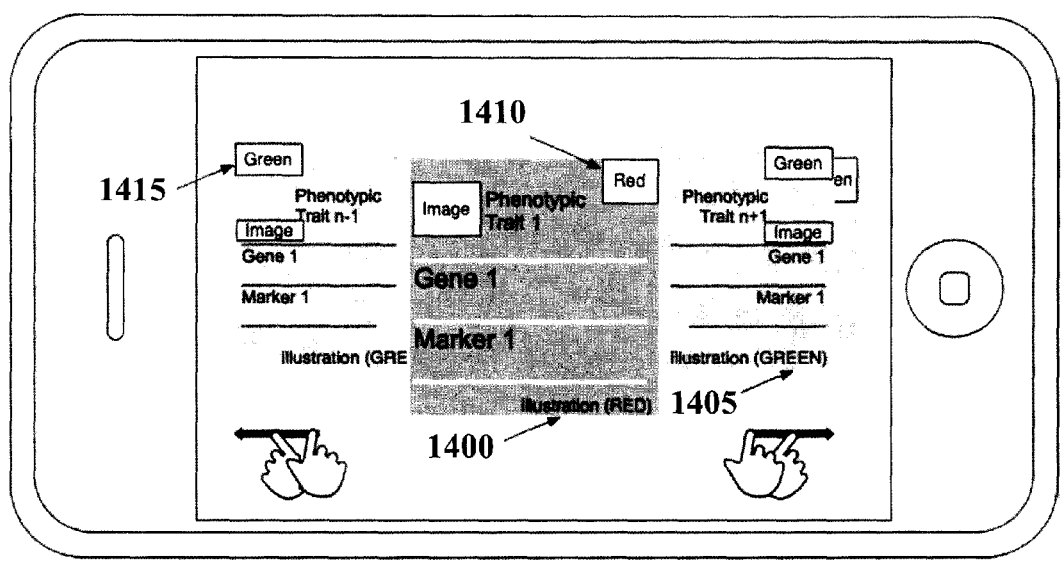
FIG. 14 shows an embodiment for the rapid identification of genomic data utility on portable devices.

FIGS. 13 and 14 show genomic data visualization in vertical or horizontal mode on computers or portable devices with the use of color codes to simply and rapidly identify clinically important phenotypic traits.

FIG. 13 shows a vertical user interface that displays a list of phenotypic trait according the methods described herein. This concept allows the use of graphic thumbnails to display phenotypic traits. By adding red tags (indication 1300) or by using red colored thumbnails for example, one can then rapidly visualize clinically important traits. Phenotypic traits that would not have clinical impact for the patient can be displayed with green tags or thumbnails for example (indication 1305). The distinction between clinically important phenotypic traits and low or less important phenotypic traits is thus facilitated by our visual and graphical display.

FIG. 14 shows that a horizontal user interface can be used to display red colored illustrations (indication 1400) for phenotypic traits with clinical impact and green colored illustrations (indication 1405) for phenotypic trait with low clinical impact or without clinical impact. It also shows that additional colored tags like thumbnail's corner (indications 1410 and 1415) can be used for additional level of information.

This procedure may allow the use of digital music applications and platform infrastructures with minimal modification. Simple images for complex genomic data can be displayed and rapidly identified according their clinical importance with simple colored tag annotations. The visualization of genomic data through graphical images on portable devices may open a new era for the manipulation and use of genomic data in the field of wireless healthcare and personalized medicine.

Accordingly more advantages are to provide an improved concept for genomic data manipulation, to provide new graphical interfaces for the visualization of genomics results and to provide new options for the use of genomic data in personalized medicine. Still further advantages will become apparent from a study of the following description and accompanying drawings.

Uses of the Methods and Portable Devices

The GUI's, methods and devices described herein can be used by any person including by patients, individuals, medical professionals including doctors, nurses, pharmacists, counselors and the like. The GUI's, methods and devices described herein can be used to schedule a medication dosage regimen, and/or monitor compliance thereof and/or to predict the efficacy of a drug and/or to predict side-effects of a drug. Tailoring dosage regimens to an individual based at least in part on genomic information is an objective of the field of personalized medicine, which may be achieved by practicing the methods described herein.

The GUI's, methods and devices described herein can be used to schedule medical appointments or consult medical specialists. Such a use may be desirable for detecting, preventing and/or treating diseases at an early stage.

The GUI's, methods and devices described herein can be used to facilitate financial transactions based on genomic information. Some goods or services may be priced differentially based on their various utilities to individuals having various genetic markers and/or phenotypes.

Another embodiment provides the use of the methods or the portable electronic devices described herein in combination with geolocation features of the portable electronic device to determine the relative contribution of genetics and environment on a phenotypic trait or disease. Until now, there has been no practical way to parse the relative contributions of genetics and environment. In some embodiments, the portable devices described herein may communicate with a public health authority such as the Centers for Disease Control to monitor in real-time the outbreak of diseases. A system whereby a large number of individuals continually report their locations and genomic information to a central database could identify environmental causes and genetic causes of various diseases.

The methods described herein can be used by at least two individuals, wherein information is shared between the individuals to create yet more embodiments. In one embodiment two individuals share genomic information via portable electronic devices in order to determine the last common ancestor shared by the individuals. In another embodiment, a male individual and a female individual share information via portable electronic devices in order to determine the probability of phenotypic traits and/or diseases being expressed in the offspring produced by the male and female individuals.

What is claimed is:

1. A graphical user interface (GUI) for displaying genomic information on a mobile device, the GUI comprising:
(a) a listing of phenotypic traits, diseases, or a combination thereof;
(b) a listing of genes; and
(c) a listing of genetic markers, wherein the genetic markers are single nucleotide polymorphisms (SNPs), micro-satellites, DNA methylation patterns, histone deacetylation patterns, or any combination thereof and wherein the genetic markers comprise metadata comprising:
(1) a default map location;
(2) a nucleotide UID; and
(3) a gene ontology,
whereby selecting a phenotypic trait or disease from list (a) displays a listing of genes and/or genetic markers correlated with the selected phenotypic trait or disease wherein the correlations are obtained from public databases and/or scientific literature and wherein a multimedia database viewable by the GUI is populated with genomic information in place of multimedia information, whereby operation of the GUI displays genomic information.

2. The GUI of claim 1, wherein the metadata further comprises one or more of:
a disease name, a phenotype, a gene name, a protein name, a chromosome, a nucleotide accession, a protein accession, a protein UID, a EC/RN number, a filter, a locus link ID, a MIM, a modification date, a property, a PubMed UID, a taxonomy ID, a text word, and a UniGene cluster number.

3. The GUI of claim 1, wherein the phenotypic traits, diseases, or a combination thereof are represented by images.

4. The GUI of claim 3, wherein the images further comprise genes and/or genetic markers correlated with the phenotypic trait or disease.

5. The GUI of claim 3, wherein the images are scrollable by touching the display of the mobile device with a vertical, horizontal, or circular motion.

6. The GUI of claim 3, wherein the images further comprise an indication when the phenotypic trait or diseases is clinically relevant in an individual.

7. The GUI of claim 6, wherein the indication is a color code.

8. The GUI of claim 1, wherein the genomic information is from an individual person.

9. The GUI of claim 1, wherein the genomic information is obtained from public databases.

10. The GUI of claim 1, wherein:
(a) an album title field is populated with a listing of phenotypic traits, diseases, or a combination thereof;
(b) an artist field is populated with a listing of genes; and
(c) a title track field is populated with a listing of genetic markers,
whereby selecting a phenotypic trait or disease from list (a) displays a listing of genes and/or genetic markers correlated with the selected phenotypic trait or disease.

11. The method GUI of claim 10, wherein the mobile device comprises one or more of:
(a) means for activating an application on the mobile device based on the genomic information; and
(b) means for integrating geolocation information of the mobile device with the genomic information.

12. The GUI of claim 10 wherein the database comprises genes, genetic markers, default map locations, nucleotide UID, and gene ontology information.

13. A portable electronic device configured to display the GUI of claim 1.

14. The portable electronic device of claim 13, wherein the device is a mobile phone, personal digital assistant (PDA), or tablet computer.

15. The portable electronic device of claim 14 comprising means to schedule medical appointments or consult medical specialists.

16. The portable electronic device of claim 14 comprising means to facilitate financial transactions based on genomic information.

17. The electronic device of claim 14 comprising means to predict the efficacy of a drug and/or to predict side-effects of a drug.

18. The portable electronic device of claim 14 comprising geolocation features to determine relative contribution of genetics and environment on a phenotypic trait or disease.

19. The portable electronic device of claim 14 comprising means to determine the probability of phenotypic traits and/or diseases being expressed in the offspring produced by a male and a female individuals.

* * * * *